United States Patent [19]

Rickwood et al.

[11] Patent Number: 5,520,853

[45] Date of Patent: May 28, 1996

[54] PHOTOCHROMIC COMPOUNDS

[75] Inventors: Martin Rickwood, Southport; Sean D. Marsden, St. Helens; John D. Hepworth, Preston; Christopher D. Gabbutt, Blackburn, all of United Kingdom

[73] Assignee: Pilkington PLC, United Kingdom

[21] Appl. No.: 284,231

[22] Filed: Aug. 2, 1994

[30] Foreign Application Priority Data

Aug. 13, 1993 [GB] United Kingdom ............ 9316858

[51] Int. Cl.$^6$ ............. G02B 5/23; C07D 311/92
[52] U.S. Cl. ............................. 252/586; 549/389
[58] Field of Search ....................... 252/586; 549/389

[56] References Cited

U.S. PATENT DOCUMENTS

| | | | |
|---|---|---|---|
| 3,627,690 | 12/1971 | Casella | 252/586 |
| 4,826,977 | 5/1989 | Heller et al. | 252/586 |
| 4,931,221 | 6/1990 | Heller | 252/586 |
| 4,980,089 | 12/1990 | Heller | 252/586 |
| 4,986,934 | 1/1991 | Kwiatkowski et al. | 252/586 |
| 4,990,287 | 2/1991 | Bennion et al. | 252/586 |
| 5,066,818 | 11/1991 | Gemert et al. | 549/389 |
| 5,106,998 | 4/1992 | Tanaka et al. | 549/331 |
| 5,200,116 | 4/1993 | Heller | 252/586 |
| 5,238,981 | 8/1993 | Knowles | 549/389 |
| 5,244,602 | 9/1993 | Van Gemert | 252/589 |
| 5,274,132 | 12/1993 | Van Gemert | 549/389 |
| 5,340,857 | 8/1994 | Van Gemert | 524/110 |

FOREIGN PATENT DOCUMENTS

| | | |
|---|---|---|
| 0246114 | 11/1987 | European Pat. Off. . |
| 0245020B1 | 11/1987 | European Pat. Off. . |
| 0350009A1 | 1/1990 | European Pat. Off. . |
| 0358774A1 | 3/1990 | European Pat. Off. . |
| 0402228A3 | 12/1990 | European Pat. Off. . |
| 0401958A2 | 12/1990 | European Pat. Off. . |
| 0489655A1 | 6/1992 | European Pat. Off. . |
| 0562915A1 | 9/1993 | European Pat. Off. . |
| 0600668A1 | 6/1994 | European Pat. Off. . |
| 2200908A | 8/1988 | United Kingdom . |
| WO88/02371 | 4/1988 | WIPO . |
| WO90/07507 | 7/1990 | WIPO . |
| WO92/01959 | 2/1992 | WIPO . |
| WO92/09593 | 6/1992 | WIPO . |
| WO93/10112 | 5/1993 | WIPO . |
| WO93/17071 | 9/1993 | WIPO . |

OTHER PUBLICATIONS

K. Yamamoto et al., Chemical Abstracts, vol. 116, No. 12, Abstract No. 116688y, Mar. 23, 1992, p. 710.

S. Yamamoto et al., Chemical Abstracts, vol. 116, No. 4, Abstract No. 31510j, Jan. 27, 1992, p. 722.

Ya. N. Malkin et al., "*Quantitative Study of the Photostability of Spiropyrans,*" J. Photochem. Photobiol. A, vol. 49, No. 1–2, 1989, pp. 75–88.

Ya. N. Malkin et al., "*Quantitative Study of the Photostability of Spiropyrans,*" vol. 39, No. 2, 1990, pp. 236–242.

T. B. Krasieva et al., "*Photochemistry of Spiropyrans of the Dithiolane Series With Polycondensed Chromene Fragments,*" vol. 38, No. 11, 1989, pp. 2297–2302.

S. M. Aldoshin et al., "*Effect of the Nature of the Heteroatoms in the Spiro Group on the Structure of Spiropyrans and an X–ray Study of Spiropyran of the Dithiolane Series $C_{17}H_{16}O_2S_2$,*" vol. 37, No. 7, 1988, pp. 1385–1387.

Vijaya Kumar et al., *Glycomaurin and Glycomaurrol, New Carbazole Alkaloids from Glycosmis mauritiana (Rutaceae) Bark*, Aust. J. Chem., 1989, 42, pp. 1375–9.

Chihiro Ito et al., *New Carbazole Alkaloids from Murraya euchrestifolia Hayata*, Chem., Pharm. Bull, 38(6), 1990, vol. 38, No. 6, pp. 1548–1550.

Chemical Abstract, *Some reactions of coumestans*, vol. 84, 1976, p. 564.

Motoi Yogo et al., *Synthesis of Some Carbazolequinone Alkaloids and Their Analogues, Facile Palladium–Assisted Intramolecular Ring Closure of Arylamino–1,4–benzoquinones To Carbazole–1,4–quinones*, Chem. Pharm. Bull, 39(2), vol. 39, No. 2, pp. 328–334.

David Creed et al., *Photochemistry of Electron –Transport Quinones. II.$^1$ Model Studies with Plastoquinone–1 [2,3–Dimethyl–5–3–methylbut–2–enyl)–4–benzoquinone]*, Journal of the American Chemical Society, 93(2), Jan. 27, 1971, pp. 502–511.

Asish De, *Studies in Sulphur Heterocycles: Part III–Syntheses of Tricyclic Compounds with Condensed Thiophene Rings*, Indian Journal of Chemistry, vol. 23B, Oct. 1984, pp. 918–925.

Yun–Cheung Kong et al., *Micromelum: a Key Genus in the Chemosystematics of the Clauseneae*, Biochemical Systematics and Ecology, vol. 16, No. 5, 1988, pp. 485–489.

*Primary Examiner*—Philip Tucker
*Attorney, Agent, or Firm*—Burns, Doane, Swecker & Mathis

[57] ABSTRACT

A naphthopyran compound of general formula (I)

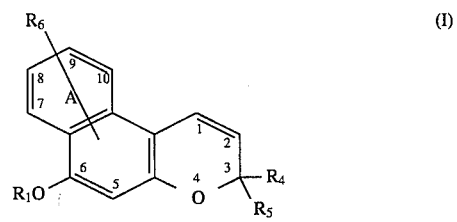

wherein $R_1$ represents an alkyl group or an aryl group;

each of $R_4$ and $R_5$, which may be the same or different, independently represents an alkyl, alkenyl, carbocyclic or heterocyclic group, or $R_4$ and $R_5$ taken together with the carbon atom to which they are attached form a carbocyclic ring or a heterocyclic ring; and $R_6$ represents a hydrogen atom or a substituent selected from alkyl, alkoxy, aryl, aryloxy, heteroaryl, halogen, amino, substituted amino, azo, imino, amide, carboxylate, ester, cyano, trifluromethyl or nitro, and in addition $R_6$ may represent a carbocyciic or heterocyclic ring fused to ring A.

The naphthopyran compounds of the invention are useful as photochromic materials in lenses, e.g. sunglasses, and photochromic transparencies for cars and aircraft.

14 Claims, No Drawings

PHOTOCHROMIC COMPOUNDS

The present invention relates to certain novel photochromic naphthopyran compounds, and to articles and compositions containing them.

Photochromism is a well-known physical phenomenon which is observed with certain classes of chemical compounds. A detailed discussion of this phenomenon can be found in "Photochromism: Molecules and Systems", Studies in Organic Chemistry 40, edited by H. Durr and H. Bouas-Laurent, Elsevier 1990.

Naphthopyran compounds as a class of compounds are known to be capable of exhibiting a photochromic effect. For example, U.S. Pat. No. 4,980,089 describes a series of photochromic naphthospiropyran compounds containing a norcamphor group or a tricyclodecane group at the 2-position of the naphthospiropyran ring (This 2-position corresponds to the 3-position of the ring in the numbering system used in the present specification).

A series of novel reversible photochromic naphthopyran compounds carrying an acetoxy group (or analogues thereof) at the 5-position of the naphthopyran ring is described in WO 92/09503.

U.S. Pat. No. 5,106,998 describes a variety of photochromic compounds including various naphthopyran compounds of different structures.

U.S. Pat. No. 5,066,818 describes a group of novel reversible photochromic naphthopyran compounds having at least one ortho-substituted phenyl group at the 3-position of the pyran ring.

In our earlier U.K. patent application No. 9306587 we describe naphthopyran compounds which provide substantially greater induced optical density in their darkened state than other known naphthopyran compounds. The common characteristic of the novel naphthopyran compounds described in our earlier U.K. patent application is that they carry a substituted amino group in the 6-position of the molecule.

We have now discovered that a similar enhanced induced optical density in the darkened state can be achieved with a group of naphthopyran compounds which carry an alkoxy or an aryloxy group in the 6-position of the molecule instead of the 6-amino substituent described in our earlier U.K. patent application. The 6-alkoxy or 6-aryloxy compounds of the present invention have a less intense induced optical density than the corresponding 6-amino compounds described in our U.K. patent application No. 9306587 but nevertheless exhibit deeper colouration in the darkened state than other known photochromic naphthopyran materials.

Accordingly, the present invention provides a naphthopyran compound of general formula (I)

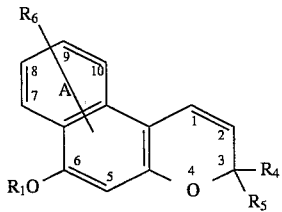

(I)

wherein $R_1$ represents an alkyl group or an aryl group;

each of $R_4$ and $R_5$, which may be the same or different, independently represents an alkyl, alkenyl, carbocyclic or heterocyclic group, or $R_4$ and $R_5$ taken together with the carbon atom to which they are attached form a carbocyclic ring or a heterocyclic ring; and $R_6$ represents a hydrogen atom or a substituent selected from alkyl, alkoxy, aryl, aryloxy, heteroaryl, halogen, amino, substituted amino, azo, imino, amide, carboxylate, ester, cyano, trifluoromethyl or nitro, and in addition $R_6$ may represent a carbocyclic or heterocyclic ring fused to ring A.

Throughout this specification, unless stated otherwise, the term "alkyl" is to be taken to mean an alkyl group having from 1 to 6 carbon atoms. Similarly, the term "alkoxy" is to be taken to mean an alkoxy group having from 1 to 6 carbon atoms.

Furthermore, in the definitions of $R_4$, $R_5$ and $R_6$ above, whenever reference has been made to a carbocyclic or heterocyclic ring (or group), unless specified otherwise it is to be understood that such carbocyclic or heterocyclic rings (or groups) may be unsubstituted or may carry one or more substituents chosen from halogen atoms, alkyl, alkoxy, aryl, aryloxy, heteroaryl, amino, substituted amino, azo, imino, amide, carboxylate, ester, cyano, trifluoromethyl or nitro groups, or, further, such rings may have one or more further rings which are fused thereto.

In the compounds of formula (I), ring A may carry more than one substituent $R_6$.

In a group of preferred compounds in accordance with the invention, the $R_1O$— substituent is a methoxy group.

Preferably, the substituents $R_4$ and $R_5$ on the pyran ring are chosen from a phenyl group, a 4-trifluoromethyl-phenyl group, a 4-alkoxyphenyl group (preferably 4-methoxyphenyl), a 2,4-di(alkoxy)phenyl group (preferably 2,4-dimethoxyphenyl) or a 4-dialkylamino-phenyl group (preferably 4-dimethylamino-phenyl).

It is also envisaged that the advantageous properties of the compounds of the present invention will be obtained with a compound of general formula (I) in which the $R_4$ and $R_5$ substituents together with the carbon atom to which they are attached form a spiro-adamantylidene group.

The naphthopyran compounds of the present invention may be prepared by a general preparative method which is based on the following reaction scheme:

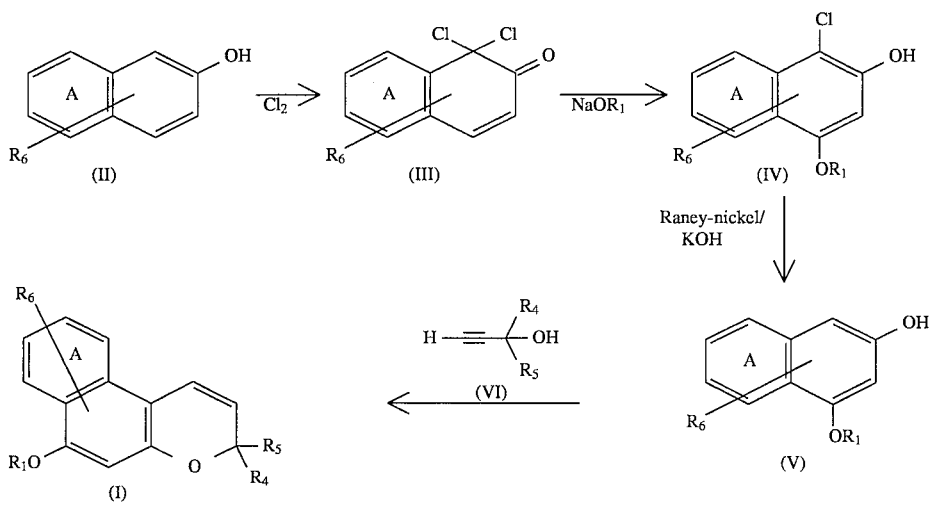

In the preparative process shown above, the 4-alkoxy/aryloxy-2-naphthol compound of formula (V) is prepared from the 2-naphthol compound of formula (II) via a series of reaction steps. Firstly, gaseous chlorination of the 2-naphthol compound of formula (II) in glacial acetic acid and an excess of sodium acetate gives the 1,1-dichloronaphth-2-one compound of formula (III) which is then reacted with sodium alkoxide/aryloxide (e.g. sodium methoxide) at 0° C. to give the 1-chloro-4-alkoxy/aryloxy-2-naphthol compound of formula (IV). Subsequent hydrodehalogenation of the chloro-naphthol (IV) with Raney-nickel in aqueous potassium hydroxide affords the 4-alkoxy/aryloxy-2-naphthol compound of formula (V). These process steps are described in more detail in a paper by G. M. Iskander et al., J. Chem. Soc. (C), 1970, 1701–3.

The final step in the preparative process is the condensation of the 4-alkoxy/aryloxy-2-naphthol compound of formula (V) with a propargyl alcohol of formula (VI) in the presence of acidic alumina (e.g. Brockmann 1 alumina), trifluoroacetic acid or other like acidic catalyst. Such condensation reactions are well known in the preparation of naphthopyran compounds and are described in detail by, for example, L. Merlini in Advances in Heterocyclic Chemistry, 1975, 18, 159 and in a number of patents, such as U.S. Pat. No. 5,066,818, U.S. Pat. No. 4,990,287, U.S. Pat. No. 4,980,089 and WO 92/09593.

Accordingly, the present invention also provides a process for preparing a naphthopyran compound of general formula (I) as defined above, which process comprises (a) chlorinating a solution of a 2-naphthol compound of general formula (II):

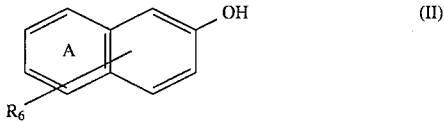

wherein A and $R_6$ are as defined above, in an organic solvent to produce the corresponding 1,1-dichloronaphth-2-one which is reacted with a sodium alkoxide/aryloxide of general formula $NaOR_1$, wherein $R_1$ is as defined above, to generate a chloro-naphthol of general formula (IV):

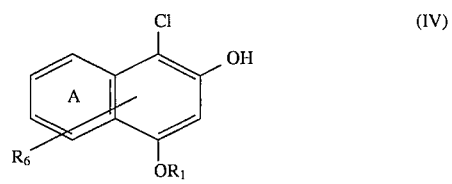

wherein A, $R_1$ and $R_6$ are as defined above, (b) subjecting the chloro-naphthol of general formula (IV) to a hydrodehalogenation reaction to produce a substituted naphthol of general formula (V):

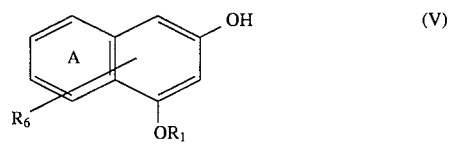

wherein A, $R_1$ and $R_6$ are as defined above, and then:

(c) condensing the substituted naphthol of general formula (V) with a propargyl alcohol of general formula (VI):

wherein $R_4$ and $R_5$ are as defined above, in the presence of acidic alumina, trifluoroacetic acid or another like acidic catalyst.

The novel naphthopyran compounds of the present invention are found to be particularly useful as photochromic materials to be incorporated into polymeric host materials so as to impart photochromic properties to the said polymeric host materials.

The photochromic naphthopyran compounds of the present invention are incorporated into the plastics host material in known manner, for example as described in European Patent No. 0245020 or U.S. Pat. No. 5,066,818.

The naphthopyran compounds of the invention exhibit substantially greater induced optical density (IOD) than prior art materials of comparable structure. As a result, the amount of photochromic material required to impart a useful degree of photochromism to a polymeric host material or to a solution is greatly reduced when compared to the amount required to obtain an equivalent photochromic effect with prior art photochromic materials. The use of reduced quantities of the photochromic materials of the invention provides a saving in cost.

The colour range of the naphthopyrans of the present invention is 410 to 500 nm; thus, the materials of the present invention impart a yellow or orange or red colouration in their darkened state. In the faded or bleached condition the materials exhibit a colourless or pale colouration.

Typical polymeric host materials are optically clear polymer materials, such as polymers of polyol(allyl carbonate)-monomers, polyacrylates such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral. Transparent copolymers and blends of the transparent polymers are also suitable as host materials. Polymers of the type described in EP 0294056 and EP 0453149 are also suitable.

Preferably, the polymeric host material is an optically clear polymerized organic material such as a polyurethane or a polymer of diethylene glycol bis(allyl carbonate) (sold under the trade name CR-39), or SPECTRALITE—a material sold by Sola Optical USA.

Usually, the amount of photochromic naphthopyran compound incorporated in the polymeric host material ranges from 0.01 to 0.5 wt %, based on the weight of the polymeric host material.

In some applications, it may be desirable or advantageous to combine the naphthopyran compounds of the present invention with other photochromic materials to obtain an aggregate colour effect. For example, spiro-oxazine materials may have a colour range of 530 to 680 nm which means that in the darkened condition the spiro-oxazines impart a red-purple or purple or blue or blue-green or green colouration to a host material. Thus, the present naphthopyran compounds are complementary to known spiro-oxazine materials such as those described in our European Patent No. 0245020, or in our UK Patent Applications Nos. 92/25346, 92/25347 and 92/25348, or to the spiro (indolino) naphthoxazines, spiro (indolino) pyrido benzoxazines and spiro (indolino) benzoxazines described in U.S. Pat. Nos. 4,637,698, 3,562,172, 3,578,602, 4,816,584, 4,215,010 and 4,342,668, and can be combined with such other photochromic materials.

Typically, when used in combination, the further additional photochromic material is present in an amount of from 0.001 to 0.5 weight %, based on the weight of the polymeric host material.

Examples of suitable uses of the photochromic plastic articles incorporating the naphthopyran compounds of the invention are in the manufacture of plano lenses, e.g. for sunglasses, and ophthalmic lenses and as photochromic transparencies for vehicles such as cars and aircraft.

The following Examples illustrate the present invention.

EXAMPLE 1

3,3-Dianisyl-6-methoxy-3H-naphtho[2,1-b]pyran.

A mixture of 4-methoxy-2-naphthol (0.26 g; 0.015 mol). 1,1-dianisylprop-2-yn-1-ol (0.40 g g;0.0015 mol), acidic alumina Brockmann 1 (3.5 g) and toluene (40.0 ml) was heated and stirred for 1.5 h, cooled, filtered. The filtrate was washed with 2M NaOH then water, dried and evaporated to give an orange gum. Trituration with hexane yielded 3,3-dianisyl-6-methoxy-3H-naphtho[2,1-b]pyran of formula (1) below as an off-white solid (41%). Crystallisation from hexane and ethylacetate gave the pyran as white microplatelets, m.pt. 158°–160° C.

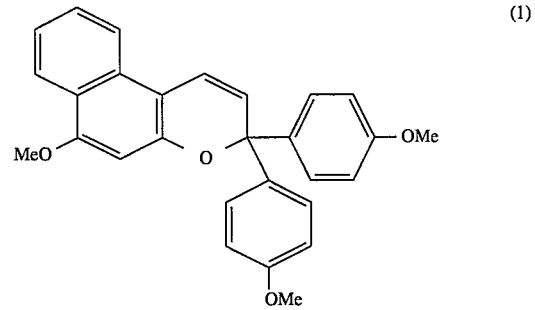

(1)

EXAMPLE 2

3-Anisyl-3-(p-trifluoromethyl)phenyl-6-methoxy-3H-naphtho [2,1-b]pyran.

A mixture of 4-methoxy-2-naphthol (0;19 g;0.0011 mol), 1-anisyl-1-(p-trifluoromethyl)phenylprop-2-yn-1-ol (0.33 g g;0.0011 mol), acidic alumina Brockmann 1 (3.5 g) and toluene (40.0 ml) was heated and stirred for 1 h, cooled then filtered. The filtrate was washed with 2M NaOH then water, dried and evaporated to give a thick orange oil. Trituration with hexane followed by recrystallisation with hexane gave 3-anisyl-3-(p-trifluoromethyl)phenyl-6-methoxy-3H-naphtho[2,1-b]pyran of formula (2) below as a white solid (20% yield), m.pt. 149°–151° C.

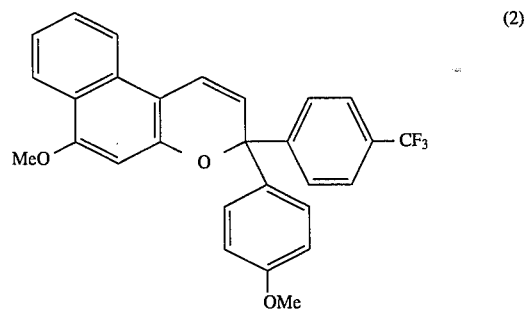

(2)

For the purposes of comparison a number of corresponding compounds having no substitution at the 6-position were also prepared. The preparation of these compounds is described in the following Comparative Examples.

Comparative Example 1

3,3-Dianisyl-3H-naphtho[2,1-b]pyran.

A mixture of 2-naphthol (3.23 g;0.0224 mol), 1,1-dianisylprop-2-yn-1-ol (6.00 g;0.0224 mol), acidic alumina Brockmann 1(6 g) and toluene (250 ml) was heated and stirred for 1.5 h, cooled, filtered and the solid washed with toluene. The filtrate was evaporated to give a pale purple tacky solid which was washed with pet. ether (40–60)/ diethyl ether to yield crude product (7.07 g). Purification of the solid by crystallisation from ethylacetate gave 3,3-dianisyl-3H-naphtho[2,1-b]pyran as a white solid (5.52 g;66% yield), m.pt 176°–177° C.

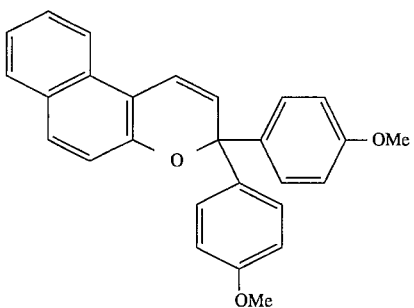

Comparative Example 2

3-Anisyl-3-(p-trifluoromethyl)phenyl-3H-naphtho[2,1-b]pyran.

A mixture of 2-naphthol (1.44 g;0.010 mol), 1-anisyl-1-(4-trifluoromethyl)phenylprop-2-yn-1-ol (3.22 g; 0.0105 mol), acidic alumina Brockmann 1 (8 g) and benzene (40.0 ml) was heated and stirred for 3 h, cooled, filtered and the solid washed with toluene. The filtrate was evaporated to give an orange oil which was chromatographed over silica (eluent: 10% ethylacetate in pet. ether (40–60)) to give a pale yellow oil which solidified on trituration with diethyl ether to yield 3-anisyl-3-(4-trifluoromethyl)phenyl-3H-naphtho[2,1-b]pyran as a white solid (1.60 g;37% yield), m.pt. 136°–137.5° C.

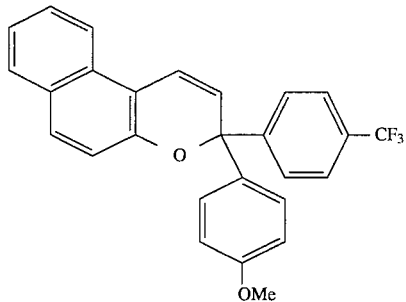

The photochromic properties of the naphthopyran compounds of the present invention were tested by preparing, in conventional manner, by a direct casting process, 2.4 mm plates of a U.V. curable plastics host material (made and sold as SPECTRALITE by Sola Optical USA) incorporating the photochromic naphthopyran in a concentration of 0.05% w/w.

Similar plates were made with samples of the comparative compounds.

The resultant plates were illuminated under standard solar simulation conditions at Air Mass 2 at 21° C. (see Parry Moon, J. Franklin Inst. 230, (1940), p 583–617). The measurements which were made on the samples in the darkened condition were taken when the samples had reached a steady state; this steady state was deemed to have been reached after 10 minutes in the darkened condition.

The results obtained are shown in Table 1 below.

TABLE 1

| | Bleached IVT | Darkened IVT | IOD $\lambda_{max}$ | $\lambda_{max}$ nm |
|---|---|---|---|---|
| Examples | | | | |
| 1 | 81.2 | 59.1 | 1.42 | 455 |
| 2 | 89.3 | 76.0 | 1.62 | 425 |
| Comparative Examples | | | | |
| 1 | 91.2 | 79.9 | 0.12 | 490 |
| 2 | 91.2 | 84.0 | 0.15 | 450 |

The results in Table 1 show the integrated visible transmission (IVT) measured in both the bleached condition and the darkened condition. These values show, for each material, the typical visual photochromic range which can be achieved.

The induced optical density at the point of maximum adsorption of the chromophore (IOD at $\lambda_{max}$) is deduced by means of the following relationship:

$$IOD \text{ at } \lambda_{max} = \log_{10} \frac{\text{Bleached } (\lambda_{max})}{\text{Darkened } (\lambda_{max})}$$

The IOD values set out in Table 1 show that the naphthopyran compounds of the present invention exhibit in their darkened condition a very much greater depth of colour than the corresponding structures in which the 6-alkoxy substituent is absent (IOD Of 1.42 as compared to IOD of 0.12; and IOD of 1.62 as compared to IOD of 0.15).

We claim:

1. A naphthopyran compound of general formula (I)

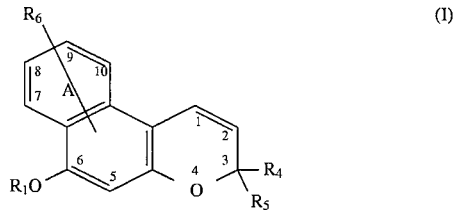

wherein $R_1$ represents an alkyl group or an aryl group; each of $R_4$ and $R_5$, which may be the same or different, independently represents an alkyl, alkenyl or carbocyclic group, or $R_4$ and $R_5$ taken together with the carbon atom to which they are attached form a carbocyclic ring; and $R_6$ represents a hydrogen atom or a substituent selected from alkyl, alkoxy, aryl, aryloxy, heteroaryl, halogen, amino, substituted amino, azo, imino, amide, carboxylate, ester, cyano, trifluromethyl or nitro, and in addition $R_6$ may represent a carbocyclic ring fused to ring A.

2. A naphthopyran compound according to claim 1, wherein the $R_1O$— substituent is a methoxy group.

3. A naphthopyran compound according to claim 1, wherein the $R_4$ and $R_5$ substituents are chosen from a phenyl group, a 4-trifluoromethylphenyl group, a 4-alkoxyphenyl group, a 2,4-di(alkoxy)phenyl group or a 4-dialkylaminophenyl group.

4. A naphthopyran compound according to claim 3, wherein the $R_4$ and $R_5$ substituents are chosen from a 4-methoxyphenyl group, a 2,4-dimethoxyphenyl group or a 4-dimethylaminophenyl group.

5. 3,3-Dianisyl-6-methoxy-3H-naphtho[2,1-b]pyran.

6. 3-Anisyl-3-(p-trifluoromethyl)phenyl-6-methoxy-3H-naphtho [2,1-b]pyran.

7. A photochromic article comprising a polymeric host material having a naphthopyran compound as defined in claim 1 incorporated therein or applied thereto.

8. A photochromic article according to claim 7, wherein the polymeric host material is selected from polymers of polyol (allyl carbonate) monomers, polyacrylates, poly(alkylacrylates), cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral.

9. A photochromic article according to claim 8, wherein the polymeric host material is a polyurethane, or a polymer of diethyleneglycol bis (allyl carbonate).

10. A photochromic article according to claim 7, wherein the amount of naphthopyran compound is from 0.01 to 0.5% by weight, based on the weight of the polymeric host material.

11. A photochromic article according to claim 7, comprising a further photochromic compound selected from spiro(indoline)naphthoxazines, spiro(indolino)pyrido benzoxazines, and spiro(indolino)benzoxazines.

12. A photochromic article according to claim 11, wherein the further photochromic compound is present in an amount of from 0.001 to 0.5% by weight, based on the weight of the polymeric host material.

13. A photochromic article according to claim 7, which is in the form of a lens.

14. A photochromic article according to claim 13, wherein the lens is an ophthalmic lens.

\* \* \* \* \*